United States Patent [19]
White

[11] Patent Number: 5,562,709
[45] Date of Patent: Oct. 8, 1996

[54] ATRIAL DEFIBRILLATOR HAVING BOTH SPECIFIC AND SENSITIVE R WAVE DETECTION

[75] Inventor: Harley G. White, Redmond, Wash.

[73] Assignee: InControl, Inc., Redmond, Wash.

[21] Appl. No.: 423,968

[22] Filed: Apr. 18, 1995

[51] Int. Cl.$^6$ ..................................... A61N 1/39
[52] U.S. Cl. ............................... 607/5; 128/705
[58] Field of Search ............... 607/5, 4, 16, 18; 128/705

[56] References Cited

U.S. PATENT DOCUMENTS

| | | | |
|---|---|---|---|
| 5,044,366 | 9/1991 | Alt | 607/18 |
| 5,279,291 | 1/1994 | Adams et al. | 607/5 |
| 5,330,504 | 7/1994 | Somerville et al. | 607/5 |
| 5,350,404 | 9/1994 | Adams et al. | 607/5 |
| 5,458,621 | 10/1995 | White et al. | 607/5 |

Primary Examiner—William E. Kamm
Assistant Examiner—Kennedy J. Schaetzle
Attorney, Agent, or Firm—Richard O. Gray, Jr.

[57] ABSTRACT

An implantable atrial defibrillator includes at least one lead for sensing electrical activity of a heart, a synchronizing stage for providing a synchronizing signal upon detection of an R wave, a timer for timing time intervals between immediately successive R waves, and a cardiovertor for cardioverting the heart when a cardiac interval is greater than a determined minimum time interval and in timed relation to a synchronizing signal. The defibrillator further includes first and second R wave detection channels, the first R wave detection channel providing the synchronizing stage with specific R wave detection, and the second R wave detection channel providing the timer with sensitive R wave detection.

11 Claims, 3 Drawing Sheets

ATRIAL DEFIBRILLATOR HAVING BOTH SPECIFIC AND SENSITIVE R WAVE DETECTION

BACKGROUND OF THE INVENTION

The present invention generally relates to an atrial defibrillator for applying cardioverting electrical energy to the atria of a human heart in need of cardioversion. The present invention is more particularly directed to a fully automatic implantable atrial defibrillator which exhibits improved safety by reducing the potential risk of induced ventricular fibrillation which may otherwise result from the delivery of cardioverting electrical energy to the atria of the heart at the wrong time or under improper conditions. More specifically, the atrial defibrillator of the present invention provides greater assurance against applying cardioverting electrical energy to the atria of the heart under conditions believed to contribute to induced ventricular fibrillation by having both specific and sensitive R wave detection.

Atrial fibrillation is probably the most common cardiac arrhythmia. Although it is not usually a life-threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart, and may even experience dizziness or even loss of consciousness.

Atrial fibrillation occurs suddenly, and many times can only be corrected by a discharge of electrical energy to the heart through the skin of the patient by way of an external defibrillator of the type well known in the art. This treatment is commonly referred to as synchronized cardioversion and, as its name implies, involves applying cardioverting or defibrillating electrical energy to the heart in synchronism with a detected depolarization activation wave (R wave) of the heart. The treatment is very painful and, unfortunately, most often only results in temporary relief for patients, lasting but a few weeks.

Drugs are available for reducing the incidence of atrial fibrillation. However, these drugs have many side effects and many patients are resistant to them which greatly reduces their therapeutic effect.

Implantable atrial defibrillators have been proposed to provide relief to patients suffering from occurrences of atrial fibrillation. Unfortunately, to the detriment of such patients, none of these atrial defibrillators have become a commercial reality.

Implantable atrial defibrillators proposed in the past have exhibited a number of disadvantages, which probably have been the cause of these defibrillators failing to become a commercial reality. Two such proposed defibrillators, although represented as being implantable, were not fully automatic, requiring human interaction for cardioverting or defibrillating the heart. Both of these defibrillators require the patient to recognize the symptoms of atrial fibrillation, with one defibrillator requiring a visit to a physician to activate the defibrillator, and the other defibrillator requiring the patient to activate the defibrillator from external to the patient's skin with a magnet.

Improved atrial defibrillators and lead systems which exhibit both automatic operation and improved safety are fully described in U.S. Pat. No. 5,282,837, issued Feb. 1, 1994, in the names of John M. Adams and Clifton A. Alferness, for "Improved Atrial Defibrillator and Method", and U.S. Pat. No. 5,350,404, issued Sep. 27, 1994, in the names of John M. Adams, Clifton A. Alferness, and Paul E. Kreyenhagen, for "Lead System for Use with an Atrial Defibrillator and Method", which patents are assigned to the assignee of the present invention and incorporated herein by reference. As disclosed in the aforementioned referenced patents, synchronizing the delivery of the defibrillating or cardioverting electrical energy to the atria with a ventricular electrical activation (R wave) of the heart is important to prevent induced ventricular fibrillation. ventricular fibrillation is a fatal arrhythmia which can be caused by electrical energy being delivered to the heart at the wrong time in the cardiac cycle, such as during the T wave of the cycle. The timing of the delivery of the cardioverting energy to a detected R wave is very helpful in avoiding a T wave of the heart.

It has further been observed that during episodes of atrial fibrillation, the cardiac rate increases to a high rate and/or becomes extremely variable. At high cardiac rates, the R wave of each cardiac cycle becomes closely spaced to the T wave of the immediately preceding cardiac cycle. This may lead to a condition known in the art as an "R on T" condition. It is now believed that such a condition can contribute to induced ventricular fibrillation even if the atria are cardioverted in timed relation to a detected R wave.

U.S. Pat. No. 5,207,219, issued May 4, 1993, to John M. Adams, Clifton A. Alferness, Kenneth R. Infinger, and Joseph M. Bocek, which patent is assigned to the assignee of the present invention and incorporated herein by reference, discloses and claims an atrial defibrillator which solves this problem. As described in the above-referenced patent, this is accomplished by interval timing prior to applying the cardioverting or defibrillating electrical energy. The time interval between immediately successive R waves is timed by an interval timer and the cardioverting or defibrillating electrical energy is applied only when the interval timer times an interval which is greater than a minimum interval. This provides protection from the increased vulnerability to ventricular fibrillation resulting from a high cardiac rate.

To support the operation of an atrial defibrillator having both R wave synchronized cardioversion and interval timing, it would appear, at least intuitively, that extremely sensitive R wave detection would be required. In doing so, the reset of the interval timer with each R wave and the cardioversion in timed relation to an R wave would be assured.

Sensitive detection of R waves is consistent with, and even preferable in association with, interval timing. However, detection of R waves with high sensitivity, in reality, is not consistent with or preferred for synchronized cardioversion. Rather, detection of R waves with high specificity is preferred. As used herein, the term "sensitivity" is meant to denote the degree of ability to detect an actual event, such as an R wave (ventricular activation) of the heart, and the term "specificity" is meant to denote the degree of ability to reject non-actual events, such as non-R waves.

In view of the foregoing, the present invention provides an atrial defibrillator having R wave detection for supporting both synchronized cardioversion and interval timing. More specifically, a sensitive R wave detector assures that every R wave is detected for resetting the interval timing. Because this R wave detector is sensitive, it may also detect, and mistake for an R wave, other electrogram features, such as large T waves or premature ventricular contractions. However, because all actual R waves will be detected, other features which may be detected would only lend to further safety of the device by also resetting the interval timer.

In addition to the sensitive R wave detector, a specific R wave detector is provided to assure that cardioversion will be performed in timed relation to only actual R waves. This specific R wave detector may be made specific to such an extent that, in addition to all non-actual R waves being rejected, some actual R waves may also go undetected for synchronization. However, because it is important that cardioversion occur in timed relation to only an actual R wave, the occasional missing of an actual R wave will only delay the cardioversion for another cycle, or perhaps a few more cycles. This short delay in cardioversion is certainly tolerable in view of the advantages obtained by such a specific R wave detector.

SUMMARY OF THE INVENTION

The invention therefore provides an atrial defibrillator which applies cardioverting electrical energy to the atria of a heart when the atria are in need of cardioversion and which has a first stage which requires specific sensing of ventricular activations of the heart and a second stage requiring sensitive sensing of ventricular activations of the heart. The atrial defibrillator includes the improvement of any R wave sensing system comprising means for sensing electrical activity of the heart, including ventricular activations of the heart, first detecting means for detecting ventricular activations from the electrical activity of the heart, the first detecting means providing the first stage with first ventricular activation detection signals and having a first sensitivity and a first specificity for detecting ventricular activations, and second detecting means for detecting ventricular activations from the electrical activity of the heart, the second detecting means providing the second stage with second ventricular activation detection signals and having a second sensitivity and a second specificity for detecting ventricular activations. The second sensitivity is greater than the first sensitivity and the first specificity is greater than the second specificity.

The invention further provides an implantable atrial defibrillator including means for sensing electrical activity of a heart, including ventricular activations of the heart, synchronizing means for providing a synchronizing signal upon receipt of a first ventricular activation detection signal, timing means for timing time intervals between immediately successive second ventricular activation detection signals, and cardioverting means for applying cardioverting electrical energy to the heart when the time between immediately successive second ventricular activation detection signals is greater than a determined minimum time interval and in timed relation to a synchronizing signal. The atrial defibrillator further includes first detecting means for detecting ventricular activations from the sensed electrical activity of the heart, the first detecting means providing the synchronizing means with first ventricular activation detection signals and having a first sensitivity and a first specificity for detecting ventricular activations, and second detecting means for detecting ventricular activations from the electrical activity of the heart, the second detecting means providing the timing means with second ventricular activation detection signals and having a second sensitivity and a second specificity for detecting ventricular activations. The second sensitivity is greater than the first sensitivity and the first specificity is greater than the second specificity.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the several figures of which like reference numerals identify identical elements, and wherein:

DETAILED DESCRIPTION OF THE PREFERRED EMBODIMENT

Figure 1:
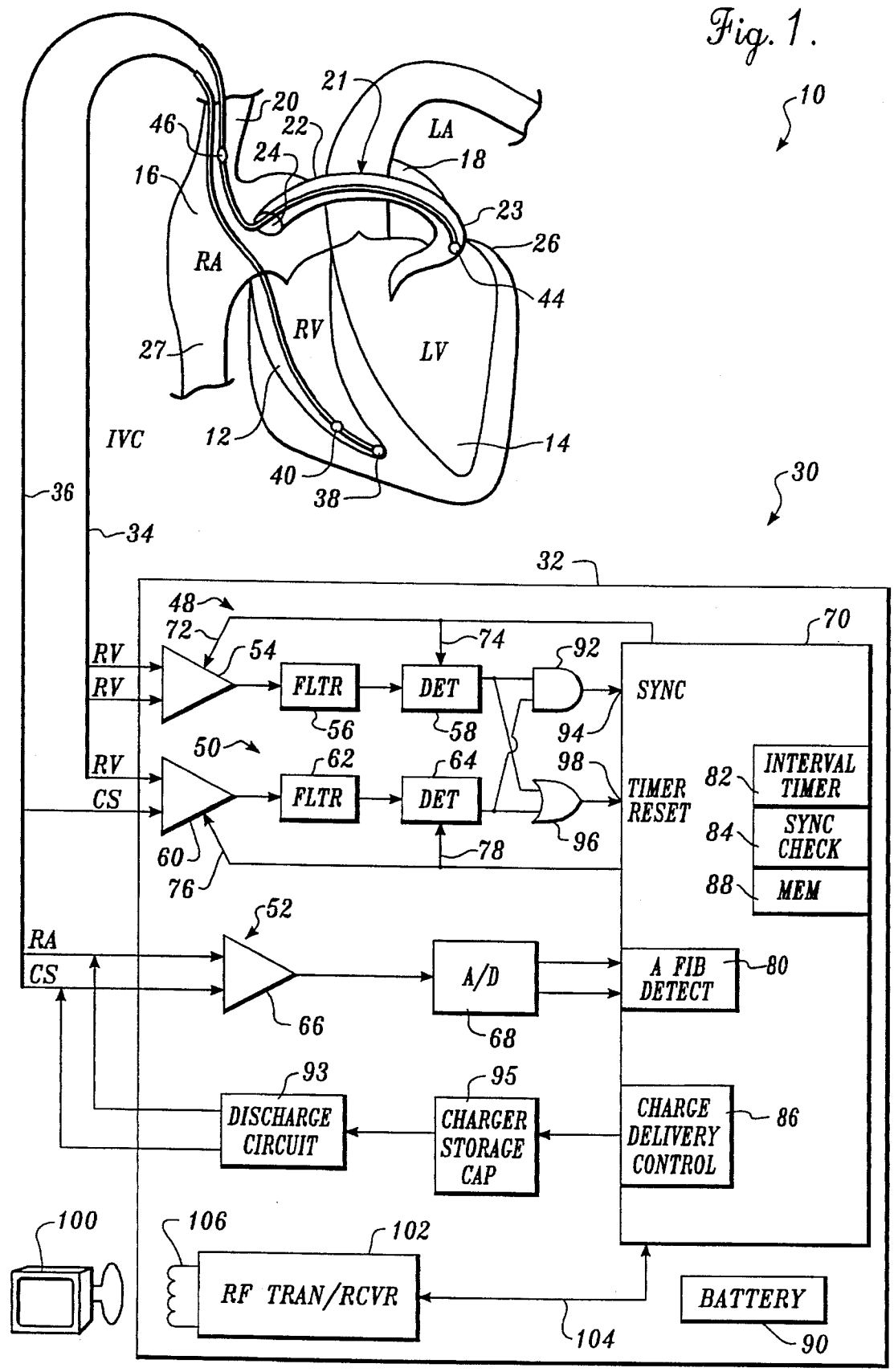
FIG. 1 is a schematic block diagram of a fully implantable atrial defibrillator embodying the present invention in accordance with the preferred embodiment thereof and shown in association with a human heart in need of atrial fibrillation monitoring and potential atrial cardioversion.

Referring now to FIG. 1, it illustrates a fully implantable atrial defibrillator 30 embodying the present invention shown in association with a schematically illustrated human heart 10 in need of atrial fibrillation monitoring and potential atrial cardioversion. The portions of the heart illustrated in FIG. 1 are the right ventricle 12, the left ventricle 14, the right atrium 16, the left atrium 18, the superior vena cava 20, the coronary sinus channel 21 which, as used herein, denotes the coronary sinus 22 and the great cardiac vein 23, the coronary sinus ostium or opening 24, the left ventricular free wall 26 and the inferior vena cava 27. In addition, as used herein, the term "ventricular activations" denotes R waves of the heart cardiac cycle which result from the cellular depolarizations of the ventricles 12 and 14.

The atrial defibrillator 30 generally includes an enclosure 32 for hermetically sealing the internal circuit elements of the atrial defibrillator 30, an endocardial first lead 34 and an intravascular second lead 36. The second lead 36 may alternatively comprise two leads. A single lead is illustrated in FIG. 1 so as to not unduly complicate the figure. The enclosure 32 and the first and second leads 34 and 36 are arranged to be implanted beneath the skin of a patient so as to render the atrial defibrillator 30 fully implantable.

The endocardial first lead 34 preferably comprises an endocardial bipolar lead having electrodes 38 and 40 arranged for establishing electrical contact with the right ventricle 12 of the heart 10. The electrodes 38 and 40 permit bipolar sensing of electrical activity of the heart, including ventricular activations in the right ventricle 12. As illustrated, the lead 34 is fed through the superior vena cava 20, into the right atrium 16, and then into the right ventricle 12.

The second lead 36 generally includes a first or distal electrode 44 and a second proximal electrode 46. As illustrated, the second lead 36 is flexible and arranged to be passed down the superior Vena cava 20, into the right atrium 16, into the coronary sinus ostium 24, and advanced into the coronary sinus channel 21 of the heart near the left side thereof. The first or distal electrode 44 is preferably within the coronary sinus 22 or the great vein 23 of the heart adjacent to the left ventricle 14. The electrode 44 is preferably elongated such that the electrode 44 is within the coronary sinus 22 and/or the great cardiac vein 23 adjacent the left ventricle 14 and beneath the left atrium 18. The second electrode 46 is also preferably elongated and located within either the right atrium 16 or the superior vena cava 20, and preferably within the right atrium 16. The elongation of the first electrode 44 and the elongation of the second electrode 46 of the second lead 36 permit these electrodes to be used for the delivery of defibrillating or cardioverting electrical energy to the atria.

Within the enclosure 32, the atrial defibrillator 30 includes a first or right ventricular (RV) detection channel 48, a second or right ventricular-coronary sinus (RVCS) detection channel 50, land an atrial sense channel 52. The RV channel 48 includes a first sense amplifier 54, a first filter 56, and a first R wave detector 58. The RVCS channel 50 includes a second sense amplifier 60, a second filter 62, and a second R wave detector 64. The atrial channel 52 includes a third sense amplifier 66, and an analog-to-digital convertor 68. Within the enclosure 32, the atrial defibrillator 30 also includes a microprocessor 70, and a memory 88.

The inputs of the first sense amplifier 54 are coupled to electrodes 38 and 40 of the first lead 34. The first sense amplifier 54 amplifies the electrical activity of the heart sensed by electrodes 38 and 40. The first sense amplifier 54 preferably includes internal filtering to precondition the electrogram signal provided by the sense amplifier 54. The first sense amplifier 54 also includes one or more gain stages. The gain of the sense amplifier 54 is controlled by the microprocessor 70 over a control line 72. The gain of the first amplifier, as will be seen hereinafter, may be selected to obtain a desired specificity and sensitivity for R wave detection in RV detection channel 48.

The purpose and function of the first filter 56 is to filter the electrogram signal provided by sense amplifier 54. The filter 56 has a first bandwidth which is selected, as described hereinafter, to obtain a desired specificity and sensitivity for R wave detection in the RV detection channel 48.

The first R wave detector 58 is coupled to the output of the first filter 56. It produces first ventricular activation detection signals upon detecting ventricular activations from the sensed electrical activity of the heart. More specifically, it produces a first ventricular activation detection signal when the input of the first R wave detector 58 exceeds a first threshold. The first threshold may be controlled by the microprocessor 70 over a control line 74 and established to provide, as will be seen hereinafter, a desired specificity and sensitivity for R wave detection in the RV detection channel 48.

The RVCS detection channel 50 preferably operates in a manner similar to the operation of the RV detection channel 48. The inputs of the second sense amplifier 60 are coupled to electrode 44 of the second lead 36 and electrode 38 of the first lead 34. The second sense amplifier 60 amplifies the electrical activity of the heart sensed by and between electrodes 38 and 44. The sense amplifier 60 also preferably includes internal filtering to precondition the electrogram signal provided by the sense amplifier 60. The second sense amplifier 60 also includes one or more gain stages. The gain of the sense amplifier 60 is controlled by the microprocessor 70 over a control line 76 and may be selected, as will be seen hereinafter, to provide a desired sensitivity or specificity for R wave detection in the RVCS detection channel 50.

The purpose and function of the second filter 62 is to filter the electrogram signal provided by sense amplifier 60. The filter 62 has a second bandwidth which is selected, as described hereinafter, to obtain a desired sensitivity and specificity for R wave detection in the RVCS detection channel 50.

The second R wave detector 64 is coupled to the output of second filter 62. It produces second ventricular activation detection signals upon detecting ventricular activation from the second electrical activity of the heart. More specifically, it produces a second ventricular activation signal when the input of the second R wave detector 64 exceeds a second threshold. The second threshold may also be controlled by the microprocessor 70 over a control line 78 and established to provide, as will be seen subsequently, a desired sensitivity or specificity for R wave detection in the RVCS detection channel 50.

The atrial sense channel 52 senses electrical activity in the atria 16 and 18 of the heart 10. To that end, the inputs of the third sense amplifier 66 are coupled to electrodes 44 and 46. The amplifier 66 preferably also includes internal filtering to precondition the electrogram signal provided by the third sense amplifier 66. This electrogram contains mainly atrial activity which is converted to digital samples by the analog-to-digital convertor 68. The digital samples are used by an atrial fibrillation detection algorithm, implemented by the microprocessor 70, to automatically detect the presence of atrial fibrillation.

The implementation of the microprocessor 70 in accordance with this embodiment of the present invention results in a plurality of functional stages. The stages include an atrial fibrillation detector 80, an interval timer 82, a synchronization stage 84, and a charge delivery and energy control stage 86. A battery 90 powers the microprocessor 70 and the other components of the defibrillator 30. The microprocessor 70 is arranged to operate in conjunction with the memory 88, which is illustrated as being internal to the microprocessor 70. However, as will be appreciated by those skilled in the art, the memory 88 may also be external to the microprocessor 70 and coupled to the microprocessor 70 by a multiple bit address and data bus. Such an arrangement may be preferred when a large amount of memory capacity is required.

For determining if the atria of the heart 10 are in need of cardioversion, the atrial defibrillator 30 stores the digital samples of an electrogram segment provided by the digital-to-analog convertor 68 in the memory 88. After the digital samples of the EGM segment are stored, they are analyzed by the atrial fibrillation detector 80 to determine if the atria are in need of cardioversion.

The atrial defibrillator 30 further includes a charger and storage capacitor circuit 95 which charges a storage capacitor to a predetermined peak voltage level and a discharge circuit 93 for discharging the storage capacitor within the circuit 95 for a predetermined time to provide a controlled discharge output or, electrical energy when required to the atria of the heart 10. To that end, the discharge circuit 93 is coupled to the first electrode 44 and the second electrode 46 of the second lead 36 for applying the cardioverting or defibrillating electrical energy to the atria.

For entering operating parameters into the microprocessor memory 88, the atrial defibrillator 30 receives programmable operating parameters from an external controller 100, which is external to the skin of the patient. The external controller 100 is arranged to communicate with a receiver/transmitter 102 within enclosure 32, which is coupled to the microprocessor 70 over a bidirectional bus 104. The receiver/transmitter 102 may be of the type well known in the art for conveying various information which it obtains from the microprocessor 70 to the external controller 100, or for receiving programming parameters from the external controller 100 which the receiver/transmitter 102 then conveys to the microprocessor 70 for storage in its memory 88.

When the atrial fibrillation detector 80 determines that the atria 16 and 18 are in fibrillation and thus in need of cardioversion, the charge delivery control 86 causes the charger and storage capacitor circuit 95 to charge the storage capacitor within the circuit 95. When certain energy delivery criteria are met, the charge delivery control 86 causes the discharge circuit 93 to discharge the capacitor of the circuit 95 for applying cardioverting electrical energy to the atria 16 and 18. As will be seen hereinafter, the energy is delivered in synchronized time relation with the first R wave detected by the first and second R wave detectors 58, 64 which completes a cardiac interval which is longer than a determined minimum time interval.

The energy delivery criteria may include morphological checks from stored electrogram data and are described, for example, in co-pending application Ser. No. 08/259,476, filed Jun. 14, 1994, in the name of the inventor herein, for "Cardioversion Synchronization System and Method for an Atrial Defibrillator", which application is assigned to the assignee of the present invention and incorporated herein by reference. The above-referenced application discloses structure for storing the electrogram data and preferred morphological criteria. The morphological analysis may be performed by the "SYNC CHECK" stage 84 illustrated in FIG. 1.

Aside from the morphological analysis, other energy delivery analysis which may be performed alone or in addition to the morphological analysis include the hardware detection of an actual R wave, and the satisfaction of the minimum interval criteria implemented by the interval timer 82. The detection of an actual R wave requires the specific detection of R waves, while the implementation of the interval timer requires the sensitive detection of R waves. As a result, in accordance with this preferred embodiment of the present invention, the RV detection channel 48 has a first sensitivity and a first specificity, the RVCS detection channel has a second sensitivity and a second specificity, and the first specificity is greater than the second specificity, while the second sensitivity is greater than the first sensitivity. This relation can be obtained by appropriately selecting, relative to each other, the gains of amplifiers 54 and 60, the bandwidths of filters 56 and 62, the thresholds of R wave detectors 58 and 64, or combinations of the foregoing. The manner in which the contrasting specificities and sensitivities are obtained will be described subsequently.

In addition to an R wave being specifically detected by the RV detection channel 48 for energy delivery to occur, it is also preferred that the same R wave be detected in the more sensitive RVCS detection channel 50. This increases the safety of the device by requiring the R wave to be detected in both the RV and RVCS detection channels 48 and 50. To that end, the inputs of AND gate 92 are coupled to both detection channels 48 and 50, and the output of AND gate 92 is coupled to a sync input 94. Hence, AND gate 92 provides a synchronization signal to input 94 in response to receiving the first ventricular activation detection signal from detector 58 and the second ventricular activation detection signal from detector 64. Because of the AND gate function of AND gate 92, the function of AND gate 92 will be dominated by the more specific detection channel, channel 48, to cause the synchronization signal to be specifically provided.

As previously explained, it is preferred that the interval timer 82 be implemented with sensitive detection of R waves. The RVCS channel 50 provides that sensitive detection. Also, it is preferable that the detection of an R wave by either RV channel 48 or RVCS channel 50 be used to reset the interval timer as disclosed, for example, in copending application Ser. No. 08/259,515, filed Jun. 14, 1994, in the names of Harley White and John Adams, for "Atrial Defibrillator and Method for Providing Dual Reset of an Interval Timer", which application is assigned to the assignee of the present invention and incorporated herein by reference. To that end, OR gate 96 has inputs coupled to both R wave detectors 58 and 64. The output of OR gate 96 is coupled to a reset input 98 for resetting the interval timer 82.

Figure 2:
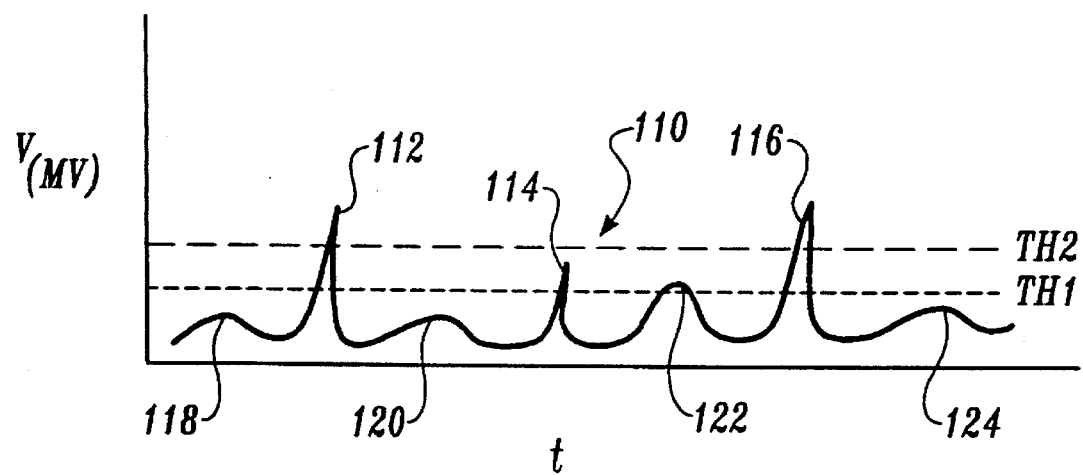
FIG. 2 is an illustration of an electrogram for demonstrating the operation of the defibrillator of FIG. 1 when configured in accordance with a first embodiment.

Referring now to FIG. 2, it illustrates how the RVCS channel 50 may be more sensitive and less specific than the RV channel 48 for detecting R waves by selecting different thresholds of detectors 64 and 58. The electrogram 110 thereshown includes R waves 112, 114 and 116, and T waves 118, 120, 122 and 124. FIG. 2 also illustrates two different thresholds, TH1 and TH2. Threshold TH1 may be the threshold of detector 64, and threshold TH2 may be the threshold of detector 58. Threshold TH1 is lower than threshold TH2 and, hence, is more sensitive because it provides a greater ability to detect R waves than threshold TH2. Threshold TH1 even results in non-R waves, such as T wave 122, being detected for resetting the interval timer While T wave 122 is not detected at threshold TH2. Hence, threshold TH2 and RV channel 48 is more specific and less sensitive than threshold TH1 and RVCS channel 50. As illustrated with threshold TH2, the only detected events are R waves 112 and 116 to provide 100% specificity. It has rejected all non-R waves. Threshold TH1 is more sensitive than threshold TH2 because it detected R wave 114 while threshold TH2 failed to detected R wave 114. The higher sensitivity obtainable with threshold TH1 is further illustrated by threshold TH1 sensing T wave 122 as an R wave, while threshold TH2 never detected T wave 122. As a result, by selecting appropriate thresholds for detectors 58 and 64, RV channel 48 can be made more specific and less sensitive than RVCS channel 50 for detecting R waves in accordance with this embodiment.

Figure 3:
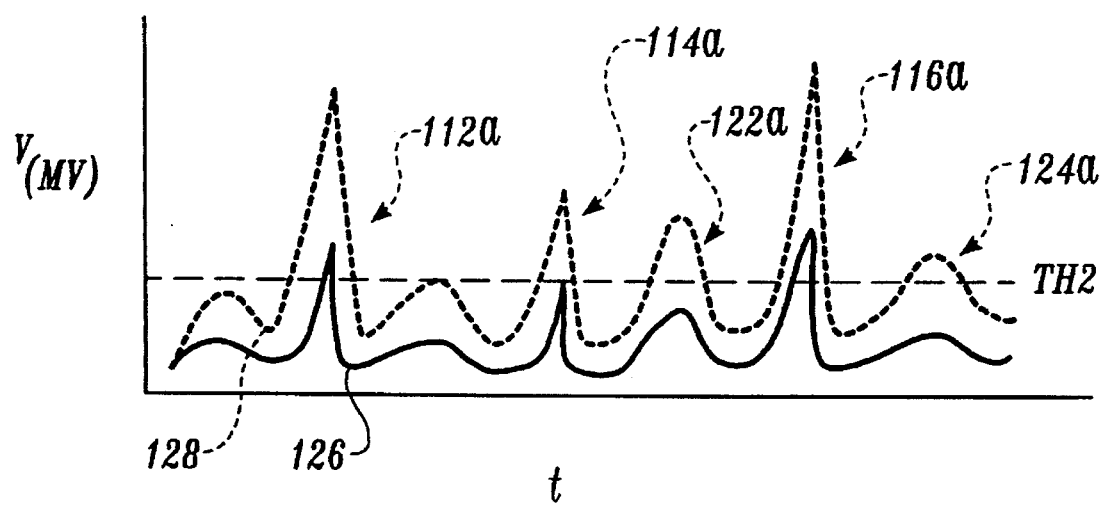
FIG. 3 is an illustration of a pair of electrograms for demonstrating the operation of the defibrillator of FIG. 1 when configured in accordance with a second embodiment.

FIG. 3 illustrates a similar relationship by selecting appropriate gains for amplifiers 54 and 60. Hence, the same threshold TH2 is shown against the electrogram 126, which represents the output of a sense amplifier due to a first gain and electrogram 128 (in dotted line), which represents the output of the same amplifier due to a second and higher gain. It will be noted that at the lower gain (electrogram 126), only R waves 112a and 116a would be detected, while at the higher gain (electrogram 128), R waves 112a, 114a and 116a, together with T waves 122a and 124a, would be detected. Hence, by selecting the gains of amplifiers 54 and 60, the RV channel 48 can be made more specific and less sensitive than RVCS channel 50 for R wave detection.

Figure 4A:
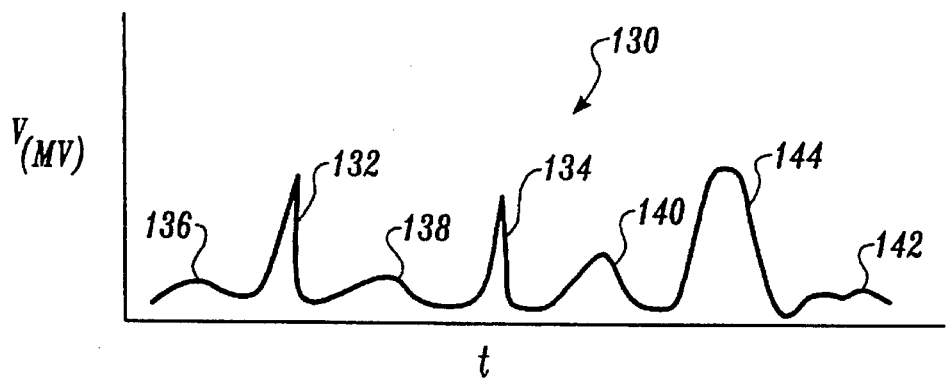
FIG. 4a is an illustration of an electrogram after having been initially filtered.
Figure 4B:
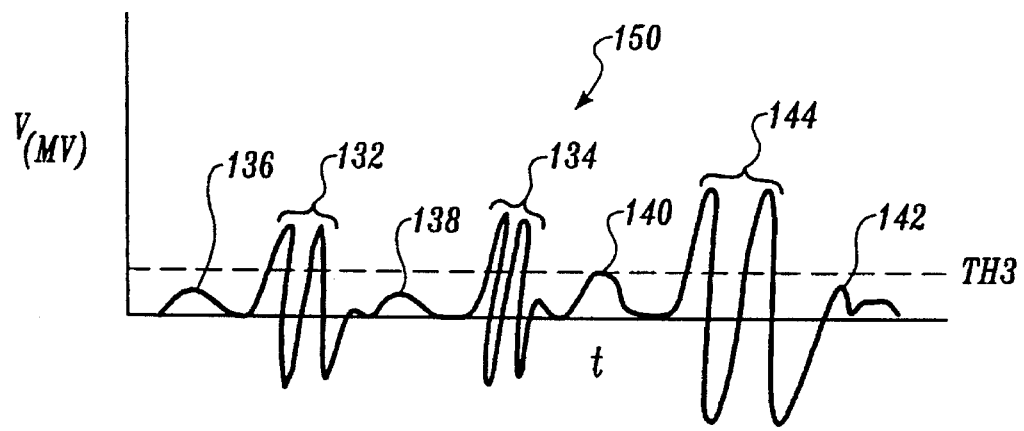
FIG. 4b is an illustration of the electrogram of FIG. 4a after further filtering with a second bandwidth; and, FIG. 4c is another illustration of the electrogram of FIG. 4a after further filtering with a first bandwidth more narrow than the second bandwidth.
Figure 4C:
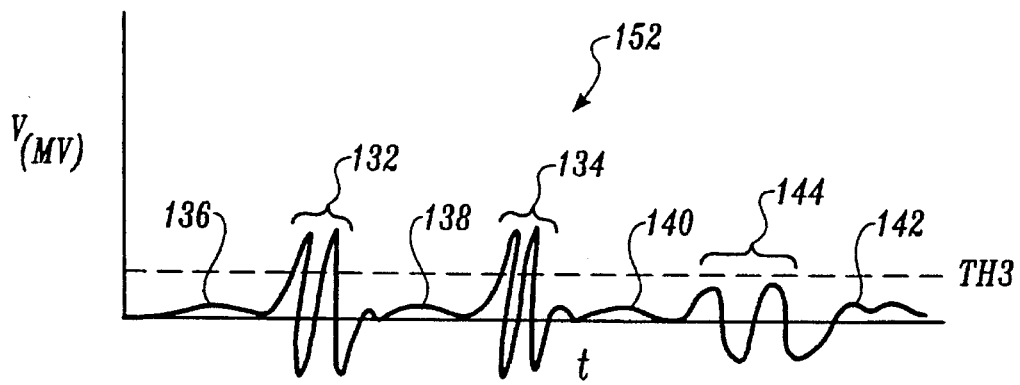

Lastly, referring to FIGS. 4a, 4b and 4c, the electrogram 130 of FIG. 4a illustrates a representative electrogram output of a sense amplifier providing prefiltering. It will be noted that electrogram 130 includes R waves 132 and 134, T waves 136, 138, 140 and 142, and a premature ventricular contraction (PVC) 144.

FIG. 4b illustrates the electrogram 130 after additional filtering with a bandwidth beginning at 10 Hertz and ending at 60 Hertz, for example. The resulting electrogram 150 includes the R waves 132 and 134, the T waves 136, 138, 140 and 142, and the PVC 144. With a detection threshold TH3, R waves 132 and 134, T wave 140, and PVC 144 would be detected.

FIG. 4c again illustrates the electrogram 130 after additional filtering, but with a bandwidth beginning at 22 Hertz and ending at 45 Hertz, which is more narrow than the bandwidth used to produce the electrogram 150 of FIG. 4b. Because of the more narrow bandwidth filtering, the resulting electrogram 152 has more highly attenuated T waves 136, 138, 140 and 142, and PVC 144. These features are attenuated to such an extent that they would not be detected at threshold TH3, leaving only R waves 132 and 134 detected. Hence, the filtering resulting in electrogram 152 of FIG. 4c provides more specific and less sensitive R wave detection than the filtering resulting in electrogram 150 of FIG. 4b. Hence, by selecting the bandwidths of filters 56 and 62, making the bandwidth of filter 56 narrower than the bandwidth of filter 62, the RV channel 48 may be made more specific and less sensitive than the RVCS channel 50 for the detection of R waves.

As can thus be seen, both specific and sensitive R wave detection is provided by the atrial defibrillator 30 in accordance with this embodiment of the present invention. Such comparative specificity and sensitivity can be obtained by appropriate selection of sense amplifier gain, R wave detector threshold, or electrogram filter bandwidth, or combinations thereof. In addition, while specific and sensitive R wave detection is performed from respective different sources of cardiac electrical activity (RV, RVCS), it will be appreciated by those skilled in the art, as contemplated by the present invention, that both specific and sensitive R wave detection may result from a single source of cardiac electrical activity. To that end, the unprocessed electrogram provided by electrodes 38 and 40 of lead 34 may be applied to both channels 48 and 50 to achieve specific R wave detection from channel 48, and sensitive R wave detection from channel 50.

While a particular embodiment of the present invention has been shown and described, modifications may be made, and it is therefore intended in the appended claims to cover all such changes and modifications which fall within the true spirit and scope of the invention.

What is claimed is:

1. In an atrial defibrillator which applies cardioverting electrical energy to the atria of a heart when the atria are in need of cardioversion and having a first stage which requires specific sensing of ventricular activations of the heart and a second stage requiring sensitive sensing of ventricular activations of the heart, the improvement comprising:

means for sensing electrical activity of the heart, including ventricular activations of the heart;

first detecting means for detecting ventricular activations from the electrical activity of the heart, the first detecting means providing the first stage with first ventricular activation detection signals and having a first sensitivity and a first specificity for detecting ventricular activations; and second detecting means for detecting ventricular activations from the electrical activity of the heart, the second detecting means providing the second stage with second ventricular activation detection signals and having a second sensitivity and a second specificity for detecting ventricular activations, the second sensitivity being greater than the first sensitivity and the first specificity being greater than the second specificity.

2. An atrial defibrillator as defined in claim 1 wherein the first and second detecting means include first and second amplifying means respectively for amplifying the sensed electrical activity of the heart, wherein the first and second amplifying means have first and second gains respectively, and wherein the second gain is greater than the first gain.

3. An atrial defibrillator as defined in claim 1 wherein the first and second detecting means include first and second ventricular activation detectors respectively, the first and second ventricular activation detectors having first and second detection thresholds respectively, and wherein the first detection threshold is greater than the second detection threshold.

4. An atrial defibrillator as defined in claim 1 wherein the first and second detecting means include first and second filter means for filtering the sensed electrical activity of the heart, wherein the first and second filter means have a first and second bandpass respectively, and wherein the first bandpass is more narrow than the second bandpass.

5. An atrial defibrillator as defined in claim 1 wherein the sensing means include first and second sensing means for sensing electrical activity of the heart between first and second pairs of locations of the heart, the first sensing means being coupled to the first detecting means and the second sensing means being coupled to the second detecting means.

6. An atrial defibrillator as defined in claim 1 further including an AND gate having inputs and an output, wherein the first and second detecting means each includes an output, wherein the outputs of the first and second detecting means are coupled to the inputs of the AND gate, and wherein the output of the AND gate is coupled to provide ventricular activation detection signals to the first stage.

7. An atrial defibrillator as defined in claim 1 further including an OR gate having inputs and an output, wherein the first and second detecting means each includes an output, wherein the outputs of the first and second detecting means are coupled to the inputs of the OR gate, and wherein the output of the OR gate is coupled to provide ventricular activation detection signals to the second stage.

8. An atrial defibrillator as defined in claim 1 wherein the first stage includes means for synchronizing the application of cardioverting electrical energy in timed relation with a ventricular activation and wherein the second stage includes means for timing time intervals between adjacent ventricular activations.

9. An atrial defibrillator as defined in claim 1 wherein the sensing means includes means for sensing electrical activity of the heart in the right ventricle of the heart.

10. An atrial defibrillator as defined in claim 1 wherein the sensing means includes means for sensing electrical activity of the heart between the right ventricle and one of the coronary sinus and great cardiac vein of the heart.

11. An implantable atrial defibrillator comprising:

means for sensing electrical activity of a heart, including ventricular activations of the heart;

synchronizing means for providing a synchronizing signal upon receipt of a first ventricular activation detection signal;

timing means for timing time intervals between immediately successive second ventricular activation detection signals;

cardioverting means for applying cardioverting electrical energy to the heart when the time between immediately successive second ventricular activation detection signals is greater than a determined minimum time interval and in timed relation to a synchronizing signal;

first detecting for detecting ventricular activations from the sensed electrical activity of the heart, the first detecting means providing the synchronizing means with first ventricular activation detection signals and having a first sensitivity and a first specificity for detecting ventricular activations; and second detecting means for detecting ventricular activations from the electrical activity of the heart, the second detecting means providing the timing means with second ventricular activation detection signals and having a second sensitivity and a second specificity for detecting ventricular activations, the second sensitivity being greater than the first sensitivity and the first specificity being greater than the second specificity.

* * * * *